United States Patent
Hung et al.

(10) Patent No.: US 8,783,120 B1
(45) Date of Patent: Jul. 22, 2014

(54) TESTING SYSTEM AND METHOD OF METAL SHEET

(71) Applicant: National Chiao Tung University, Hsinchu (TW)

(72) Inventors: Chinghua Hung, Hsinchu (TW); Yan-Yo Chen, Tainan (TW); Yu-Chung Tsai, Taoyuan County (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 13/860,924

(22) Filed: Apr. 11, 2013

(30) Foreign Application Priority Data

Jan. 7, 2013 (TW) .............................. 102100410 U

(51) Int. Cl.
*G01L 1/02* (2006.01)
*G01L 15/00* (2006.01)
*G01N 3/12* (2006.01)

(52) U.S. Cl.
CPC ....................................... *G01N 3/12* (2013.01)
USPC .................................................... 73/862.581

(58) Field of Classification Search
USPC .................................................... 73/862.581
See application file for complete search history.

(56) References Cited

U.S. PATENT DOCUMENTS 4,472,955 A * 9/1984 Nakamura et al. ................. 72/57
4,658,362 A * 4/1987 Bhatt ............................. 700/145

FOREIGN PATENT DOCUMENTS

CN          200944085 Y  *  9/2007

OTHER PUBLICATIONS

Chen, Yan-Yo, Development and Study on Integrated Apparatus of Metal Sheet Bulge Test with Forming Limit Diagram, Jul. 7, 2012, the invent is published for the thesis for the master degree, National Chiao Tung University.

* cited by examiner

*Primary Examiner* — Max Noori
*Assistant Examiner* — Jamel Williams
(74) *Attorney, Agent, or Firm* — Bacon & Thomas, PLLC

(57) ABSTRACT

The present invention provides a testing system of metal sheet, and the system at least comprises a clipping apparatus, a hydraulic press apparatus and a measuring apparatus. The clipping apparatus comprises a first mold, a second mold and a hyperelastic plate. The hydraulic press apparatus connects to the clipping apparatus and transfer a hydraulic pressure via the second mold to the one of the testing sheet set to let it bulge along an orientation toward the first mold. The measuring apparatus connects with the clipping apparatus and the hydraulic press apparatus separately to measure a momentary pressure of the hydraulic pressure and the bulge height of the one of the testing sheet set. A testing method using the above-mentioned system is also disclosed in the present invention.

7 Claims, 5 Drawing Sheets

TESTING SYSTEM AND METHOD OF METAL SHEET

BACKGROUND OF THE INVENTION

1. Field of the Invention

The present invention relates to a testing system of metal sheet, particularly to a testing system integrating the hydraulic bulge test and forming limit experiment equipment and the testing method.

2. Description of the Prior Art

The metal sheet has already been widely applied to different fields in industrial manufacturing, such as packaging, automotive making, consumer electronics producing, etc. The material expense is the main cost for the product manufacturing process. In order to reduce the production cost, the most direct method is to reduce the use of material. However, reducing the use of material will influence the mechanical strength of the products. Thus, in order to maintain the strength of product and reduce the material cost, it must understand the properties of the material first, and then find the most appropriate material in accordance with its applicable range and use state.

To obtain the mechanical properties of the metal sheet, the most extensive testing methods are the tensile experiment and forming limit experiment. However, two kinds of testing machine and several testing sheets should be used for the tensile experiment and forming limit experiment respectively, which will increase the complexity and cost of testing.

SUMMARY OF THE INVENTION

Thus, the present invention provides a testing system of metal sheet to integrate several tests for the mechanical property of the metal sheet. The above-mentioned system comprises a clipping apparatus, a hydraulic press apparatus and a measuring apparatus. The clipping apparatus comprises a first mold, a second mold and a hyperelastic plate. The first mold and the second mold are capable of clipping one of a testing sheet set, and the hyperelastic plate is detachable disposed between the one of the testing sheet set and the second mold. The hydraulic press apparatus connects to the clipping apparatus and transfer a hydraulic pressure via the second mold to the one of the testing sheet set to let it bulge along an orientation toward the first mold. The measuring apparatus connects with the clipping apparatus and the hydraulic press apparatus separately to measure a momentary pressure of the hydraulic pressure and the bulge height of the one of the testing sheet set.

In an embodiment of the present invention, the abovementioned measuring apparatus comprises a first sensor and a second sensor. When the first mold and the second mold clip the testing sheet, and the hydraulic press apparatus applies the hydraulic pressure on the testing sheet continuously, the first sensor measures the bulge height of the testing sheet, and the second sensor measures the momentary pressure of the hydraulic pressure. At this time, the measuring apparatus calculates a datum in accordance with the bulge height and the momentary pressure (called the first datum for easy identification).

In an embodiment of the present invention, there are several grids disposed on the testing sheet. When the testing sheet is broken by continuous application of the hydraulic pressure, the change of grid on the testing sheet can be measured (called the second datum for easy identification).

Another purpose of the present invention is to provide a testing method by using the abovementioned system. This method comprises the following steps: Firstly, using the first mold and the second mold to clip a testing sheet, then, disposing the hyperelastic plate between the testing sheet and the second mold is carried out. The hydraulic press apparatus provide the hydraulic pressure to bulge the testing sheet. Then, using the measuring apparatus to measure the bulge height of the testing sheet and the momentary pressure of the hydraulic pressure, collecting the bulge height and the momentary pressure, and calculating the first datum in accordance with the bulge height and the momentary pressure is carried out. Wherein, the first datum corresponds to a stress-strain relationship of the metal sheet.

In an embodiment of the present invention, the testing method of metal sheet provided by the present invention further comprises the following steps: Firstly, using the first mold and the second mold to clip a testing sheet with a plurality of grids. The hydraulic press apparatus provides the hydraulic pressure to the testing sheet to bulge it until it is broken. Then, measure the change amount of these grids on the testing sheet to obtain a second datum for drawing the forming limit diagram of the metal sheet.

The advantage and spirit of the present invention can be understood further by the following detail description of invention and attached Figures.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
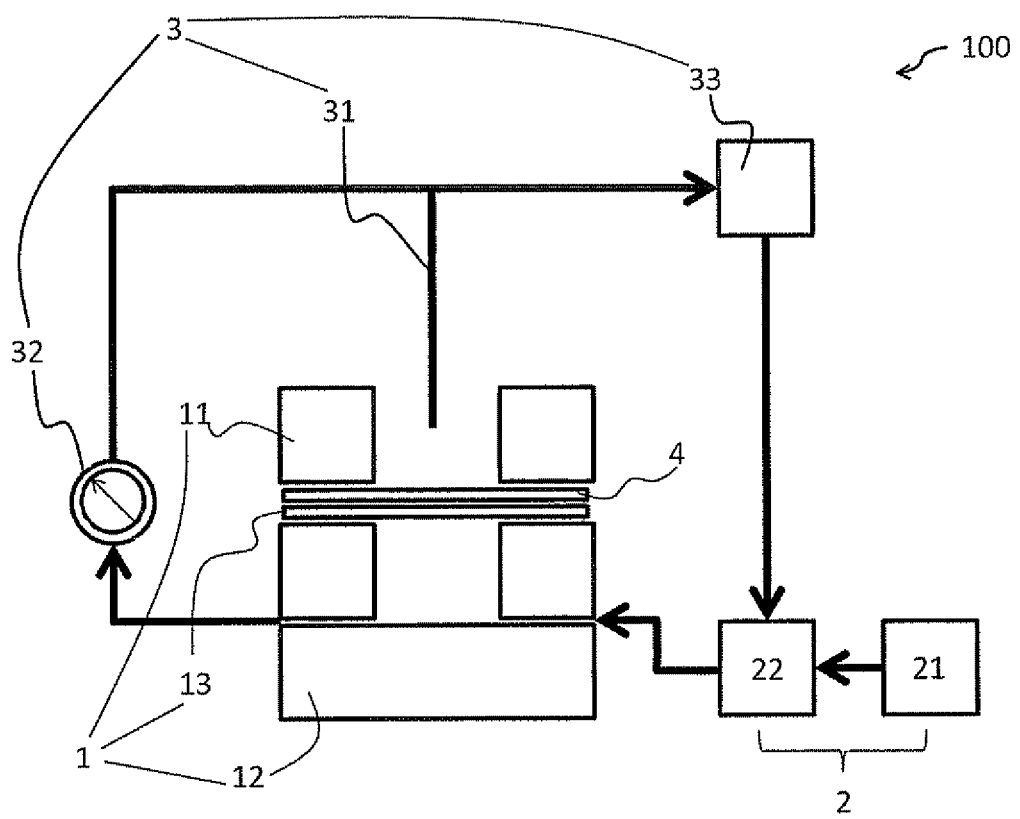
FIG. 1 shows the testing system of metal sheet according to the preferred embodiment of the present invention.
Figure 2:
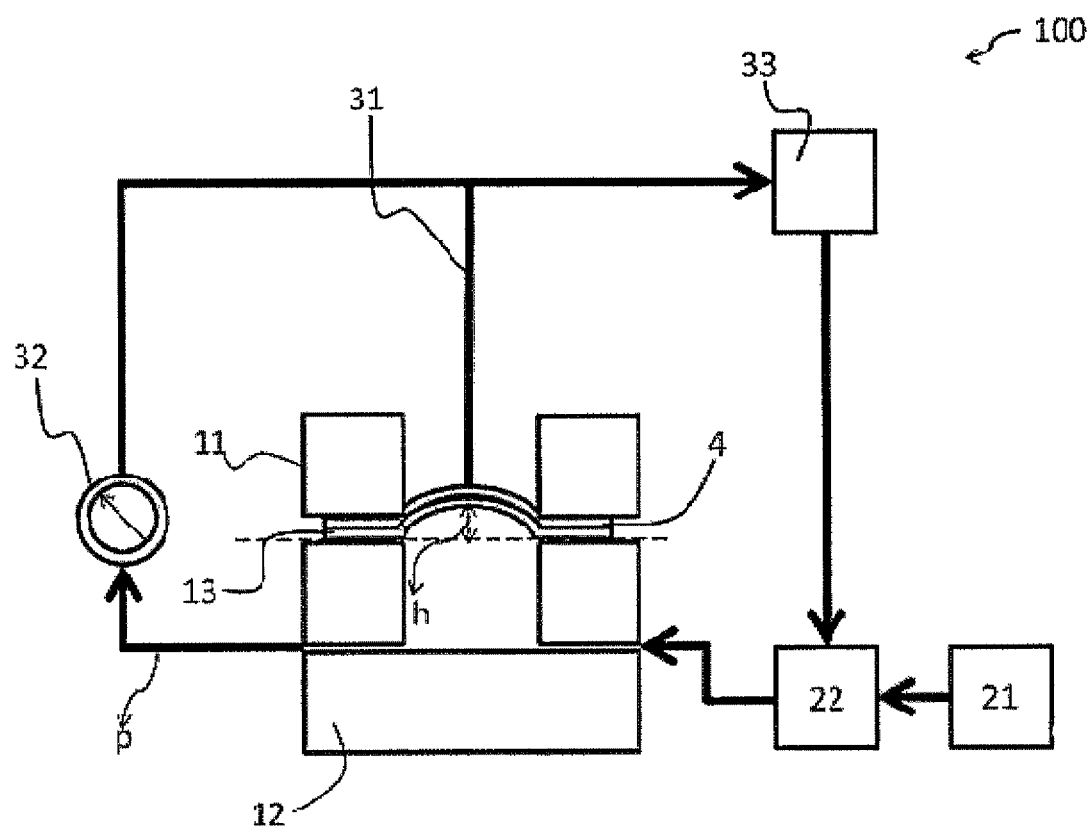
FIG. 2 shows the testing system of metal sheet according to the preferred embodiment of the present invention.

Please refer to FIG. 1 and FIG. 2. FIG. 1 and FIG. 2 show the testing system 100 of metal sheet according to the preferred embodiment of the present invention. The testing system 100 of metal sheet comprises a clipping apparatus, a hydraulic press apparatus 2 and a measuring apparatus 3. The clipping apparatus comprises a first mold 11, a second mold 12 and a hyperelastic plate 13, and the hyperelastic plate 13 is detachable disposed between the first mold 11 and the second mold 12.

As shown in FIG. 1, the hydraulic press apparatus 2 possesses a hydraulic power unit 21, and a proportional relief valve 22. The proportional relief valve 22 connects to the second mold 12 of the clipping apparatus 1. As shown in FIG. 2, when the experiment is commenced, the hydraulic power unit 21 is activated. The proportional relief valve 22 transfers the liquid into the second mold 12 and apply a hydraulic pressure to one of the testing sheet set 4 to let it bulge along an orientation toward the first mold 11. When the hydraulic press apparatus transfers the liquid into the second mold 12, the hyperelastic plate 13 is bulged by the hydraulic pressure, and the pressure is evenly transmitted to one of the testing sheet set 4. Then the bulged hyperelastic plate 13 forces the one of the testing sheet set 4 to bulge.

As shown in FIG. 1, the testing sheet set 4 comprises a plurality of testing sheets with different geometry and corresponds to the metal sheet to be tested. It means that the testing sheets with the same property (such as same material and same thickness) are used for the following test to know the mechanical property of metal sheet for industrial design.

The measuring apparatus 3 shown in FIG. 1 connects with the clipping apparatus 1 and the hydraulic press apparatus 2 separately to measure the momentary pressure of the hydraulic pressure and the bulge height h of one of the testing sheet set 4. In a preferred embodiment of the present invention, the measuring apparatus 3 comprises a first sensor 31, a second sensor 32 and a control and analysis unit 33. Preferably, the first sensor 31 is a displacement sensor. When the first mold 11 and the second mold 12 clip one of the testing sheet set 4, and the hydraulic press apparatus 2 provides the hydraulic pressure to the testing sheet continuously, the first sensor 31 measures the bulge height h of the testing sheet. The second sensor 32 is a pressure sensor, which connects with the second mold 12 to measure the momentary pressure P of the hydraulic pressure. Finally, the control and analysis unit 33 collects the bulge height h and the momentary pressure P to calculate a first datum. The calculation procedure and operation detail will be described in the following text.

After the testing system of metal sheet is installed, another purpose of the present invention is to provide a testing method for the abovementioned testing system. Firstly, conducting a hydraulic pressure bulge experiment is used to understand the stress-strain relationship of the metal sheet to be tested. The measuring apparatus 3 shown in FIG. 1 is used to measure the pressure (P) and the bulge height (h) first. The use equation (1) and equation (2):

$$\rho = \frac{(R + r_f)^2 + h^2 - 2r_f h}{2h} \quad (1)$$

$$t = t_0 \left[ \frac{R/\rho}{\sin^{-1}(R/\rho)} \right]^2 \quad (2)$$

Calculate the curvature radius $\rho$ and the dome thickness t. Place them into equation (3) and equation (4) to obtain the stress-strain relationship.

$$\bar{\sigma} = \frac{p\rho}{2t} \quad (3)$$

$$\bar{\varepsilon} = -\varepsilon_3 = \ln\left(\frac{t}{t_0}\right) \quad (4)$$

Figure 3:
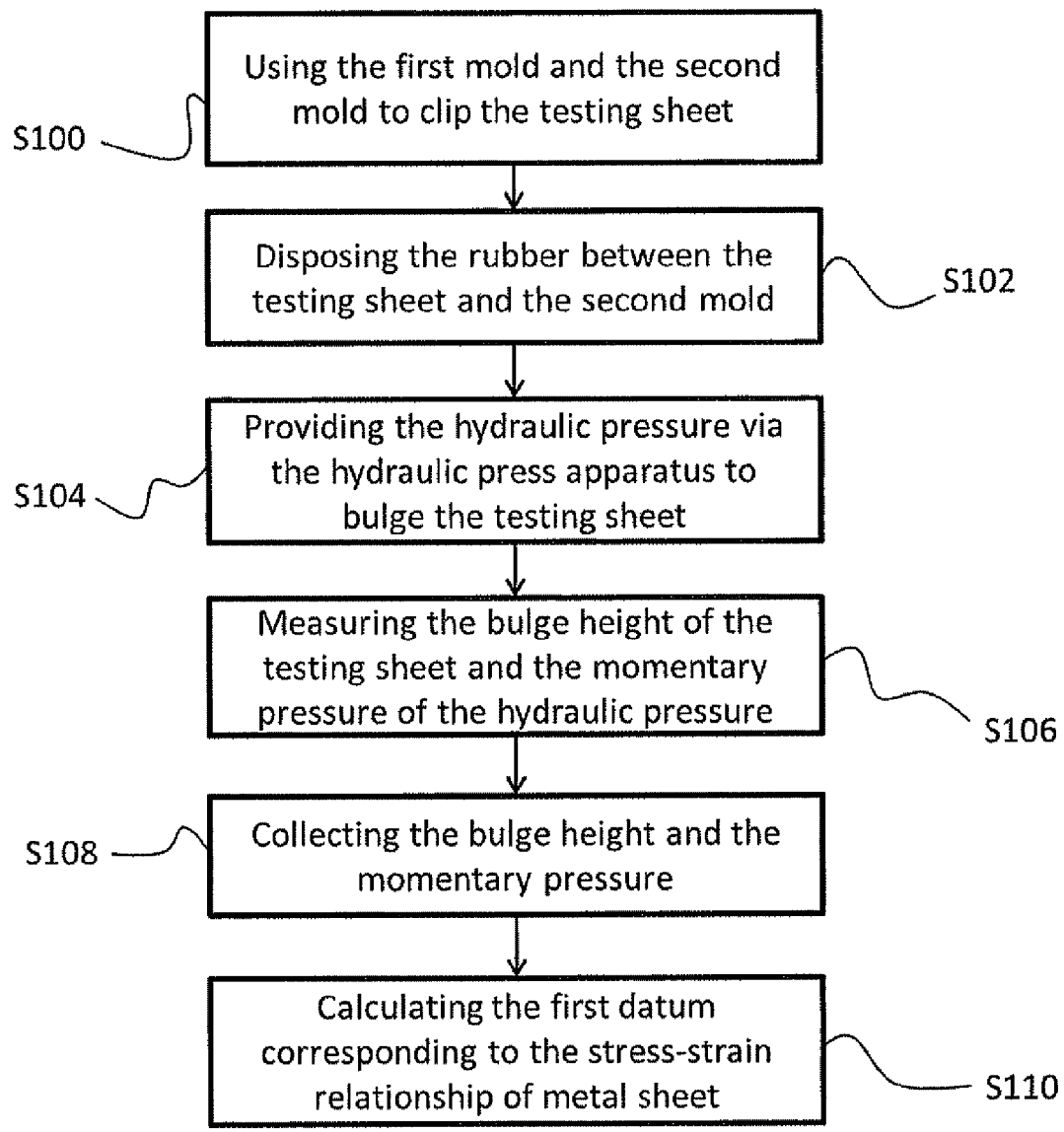
FIG. 3 shows the flow diagram for calculation the first datum of a testing system of metal sheet according to the preferred embodiment of the present invention.

Please refer to FIG. 3. FIG. 3 shows the flow diagram for calculating the first datum of a testing system of metal sheet according to a preferred embodiment according of the present invention. As shown in FIG. 3, the steps of the abovementioned testing method comprise:

Firstly, using the first mold 11 and the second mold 12 to clip the testing sheet (S100) is carried out. Then, disposing the hyperelastic plate 13 between the testing sheet and the second mold 12 (S102), and providing the hydraulic pressure via the hydraulic press apparatus 2 to bulge the testing sheet (S104). Measuring the bulge height of the testing sheet and the momentary pressure of the hydraulic pressure is carried out (S106). Collecting the bulge height and the momentary pressure (S108), and calculating the first datum corresponding to the stress-strain relationship of metal sheet (S110) is carried out.

Then, the testing system of metal sheet provided by the present invention may be the single equipment. After the actual stress-strain relationship of metal sheet is obtained by the hydraulic pressure bulge experiment, a forming limit experiment may be conducted further. The testing sheet set with a plurality of grids is used. After the hydraulic pressure is applied to the testing sheet until it is broken, measure the change amount of these grids on the testing sheet to obtain a second datum (the forming limit diagram).

Figure 4:
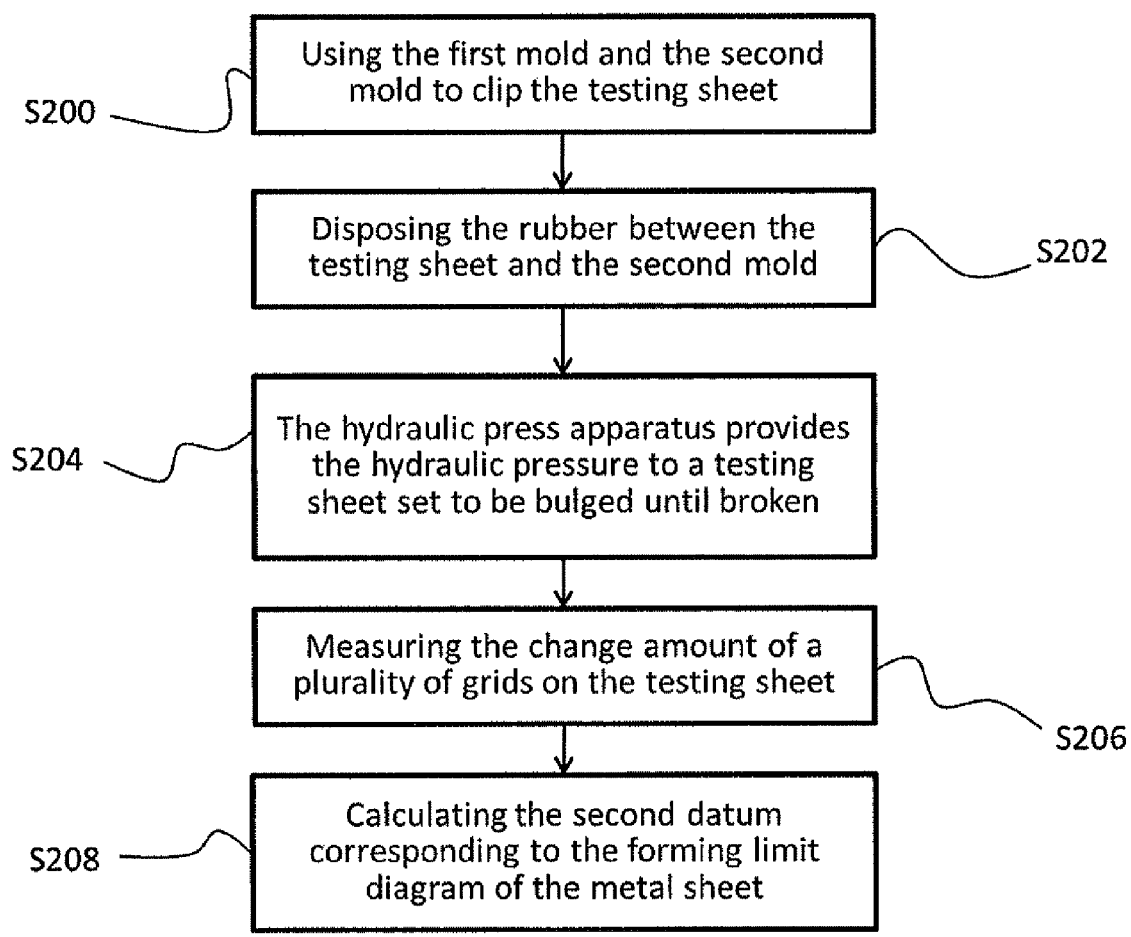
FIG. 4 shows the flow diagram for calculation the second datum of a testing system of metal sheet according to the preferred embodiment of the present invention.

Please refer to FIG. 4. FIG. 4 shows the flow diagram for calculating the second datum of a testing system of metal sheet according to a preferred embodiment according of the present invention. As shown in FIG. 4, the steps of the abovementioned testing method comprise:

Firstly, using the first mold 11 and the second mold 12 to clip the testing sheet (S200) is carried out. Then, disposing the hyperelastic plate 13 between the testing sheet and the second mold 12 (S202). The hydraulic press apparatus 2 provides the hydraulic pressure to a testing sheet set to bulge it until it is broken (S204). Then, measure the change amount of these grids on the testing sheet (S206) to obtain a second datum (S208) for drawing the forming limit diagram of the metal sheet.

As the steps shown in FIG. 4, in another embodiment, the hyperelastic plate 13 between the testing sheet and the second mold can be detached, so that the hydraulic pressure provided by the hydraulic press apparatus 2 can be applied to the testing sheet directly until it is broken (S204). The hydraulic press apparatus provides the hydraulic pressure to a testing sheet set to bulge it until it is broken. Then, measure the change amount of these grids on the testing sheet to obtain a second datum for drawing the forming limit diagram of the metal sheet.

Figure 5:
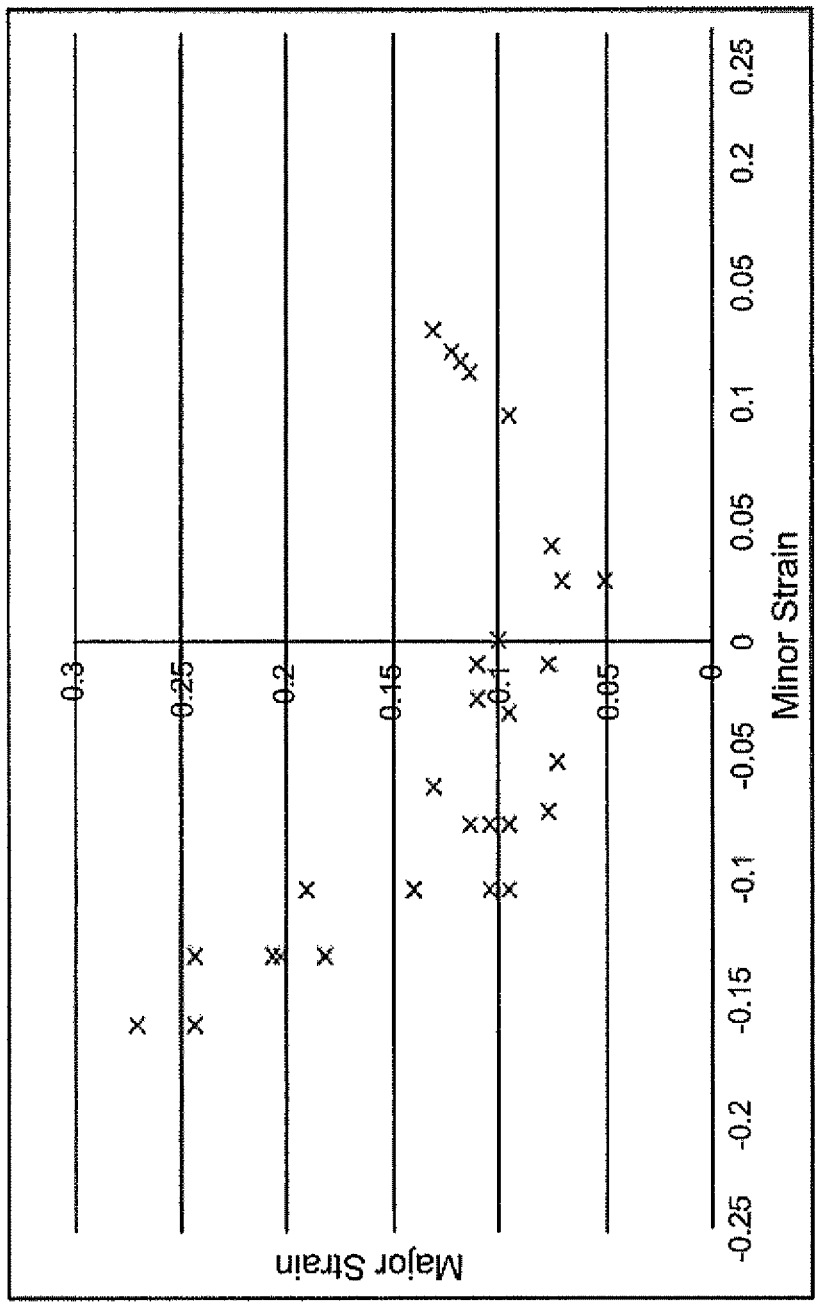
FIG. 5 shows the forming limit diagram for the testing sheet set after the hydraulic pressure is applied in a testing system of metal sheet according to the preferred embodiment of the present invention.

FIG. 5 shows the forming limit diagram for the testing sheet set after the hydraulic pressure is applied in a testing system of metal sheet according to the preferred embodiment of the present invention.

In summary, the present invention provides a testing system of metal sheet, which uses the hyperelastic plate to transmit the hydraulic pressure to integrate the hydraulic pressure bulge experiment and the forming limit experiment of metal sheet. The system provided by the present invention successfully creates a single experiment equipment to get the stress-strain curve and the forming limit diagram of the metal sheet, and reducing the complexity and cost of testing effectively.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. The testing system of metal sheet for integrating the testing for a plurality of mechanical properties of metal sheet, comprising:
    a clipping apparatus having a first mold, a second mold and a hyperelastic plate, wherein the first mold and the second mold being capable for clipping one of a testing sheet set of a metal sheet, and the hyperelastic plate being detachable disposed between one of the testing sheet set and the second mold;

a hydraulic press apparatus connecting to the clipping apparatus and transferring a hydraulic pressure via the second mold to the one of the testing sheet set to let the testing sheet set bulge along an orientation toward the first mold; and a measuring apparatus connecting with the clipping apparatus and the hydraulic press apparatus separately to measure a momentary pressure of the hydraulic pressure and a bulge height of the one of the testing sheet set.

2. The system according to claim 1, wherein an area of the hyperelastic plate is not less than one of the testing sheet set evenly transmits the hydraulic pressure to one of the testing sheet set.

3. The system according to claim 1, wherein the measuring apparatus comprises a first sensor, a second sensor, when the first mold and the second mold clip one of the testing sheet set, and the hydraulic press apparatus provides the hydraulic pressure to the testing sheet continuously, the first sensor measures the bulge height of the testing sheet, the second sensor connects with the second mold to measure the momentary pressure of the hydraulic pressure, the measuring apparatus calculates a first datum in accordance with the bulge height and the momentary pressure.

4. The system according to claim 3, wherein the testing sheet possesses a plurality of grids, after the hydraulic pressure is applied to the testing sheet until it is broken, measure the change amount of the plurality of grids on the testing sheet to obtain a second datum.

5. A testing method for the testing system of metal sheet according to claim 1, comprising:

using a first mold and a second mold to clip a testing sheet;

disposing a hyperelastic plate between the testing sheet and the second mold, wherein the hydraulic press apparatus providing a hydraulic pressure to the testing sheet to be bulged;

measuring a bulge height of the testing sheet and a momentary pressure of the hydraulic pressure;

collecting the bulge height and the momentary pressure; and calculating a first datum in accordance with the bulge height and the momentary pressure, and the first datum corresponding to a stress-strain relationship of the metal sheet.

6. The testing method according to claim 5, further comprising:

using the first mold and the second mold to clip a testing sheet;

the hydraulic press apparatus providing a hydraulic pressure to a testing sheet to be bulged until the testing sheet broken; and measuring a change amount of a plurality of grids on the testing sheet to obtain a second datum for drawing a forming limit diagram of the metal sheet.

7. The testing method according to claim 5, further comprising:

detaching a hyperelastic plate;

using a first mold and a second mold to clip a testing sheet;

providing a hydraulic pressure to a testing sheet to be bulged until the testing sheet is broken; and measuring a change amount of a plurality grids on the testing sheet to obtain a second datum for drawing a forming limit diagram of the metal sheet.

* * * * *